(12) United States Patent
Nagai et al.

(10) Patent No.: US 7,092,078 B2
(45) Date of Patent: Aug. 15, 2006

(54) FLOW CYTOMETER FOR CLASSIFYING LEUKOCYTES AND METHOD FOR DETERMINING DETECTION ANGLE RANGE OF THE SAME

(75) Inventors: Yutaka Nagai, Tokyo (JP); Kazuo Yamagishi, Tokyo (JP); Tomonobu Maruyama, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 298 days.

(21) Appl. No.: 10/402,133

(22) Filed: Mar. 31, 2003

(65) Prior Publication Data

US 2004/0189977 A1   Sep. 30, 2004

(51) Int. Cl.
*G01N 33/48* (2006.01)

(52) U.S. Cl. ...................................................... 356/39

(58) Field of Classification Search ................. 356/40, 356/39
See application file for complete search history.

(56) References Cited

U.S. PATENT DOCUMENTS

| | | | |
|---|---|---|---|
| 3,740,143 A | 6/1973 | Groner et al. | |
| 3,781,112 A | 12/1973 | Groner et al. | |
| 4,038,556 A | 7/1977 | Auer et al. | |
| 5,125,737 A * | 6/1992 | Rodriguez et al. | 356/39 |
| 5,747,343 A | 5/1998 | Tsuchiya et al. | |
| 6,084,670 A | 7/2000 | Yamazaki et al. | |
| 6,232,125 B1 * | 5/2001 | Deka et al. | 436/63 |
| 6,320,656 B1 | 11/2001 | Ferrante et al. | |
| 6,869,569 B1 * | 3/2005 | Kramer | 422/73 |
| 2003/0030783 A1 * | 2/2003 | Roche et al. | 356/39 |

FOREIGN PATENT DOCUMENTS

| | | |
|---|---|---|
| JP | 53-29794 | 3/1978 |
| JP | 57-30221 B2 | 6/1982 |
| JP | 57-33050 B2 | 7/1982 |
| JP | 58-43687 B2 | 9/1983 |
| JP | 61-221633 A | 10/1986 |
| JP | 2-3458 B2 | 1/1990 |
| JP | 2-20053 B2 | 5/1990 |

(Continued)

OTHER PUBLICATIONS

L.W.M.M. Terstappen, et al., Four-Parameter White Blood Cell Differential Counting Based on Light Scattering Measurements:, Cytometry 1988, Aug. 27, 1987, pp. 39-43.

(Continued)

*Primary Examiner*—Gregory J. Toatley, Jr.
*Assistant Examiner*—Roy M. Punnoose
(74) *Attorney, Agent, or Firm*—Sughrue Mion, PLLC

(57) ABSTRACT

A blood sample containing leukocytes flows through a flow cell. A light source emits a light beam in a first direction. The light beam incident into the flow cell is scattered by the blood sample as scattered light. A first detector detects an intensity of forward small scattered light out of the scattered light. The first detector is arranged so as to have a maximum angle of a detection angle range for the forward small scattered light stemmed from the first direction at a position inside (outside) of the flow cell, which is 3.1 (4) degrees or less. A second detector detects an intensity of forward large scattered light out of the scattered light. The second detector is arranged so as to have a detection angle range for the forward large scattered light stemmed from the first direction at a position inside (outside) of the flow cell, which falls in a range from 8 to 12 (10 to 16) degrees. A processor classifies the leukocytes based on the detected intensity of the forward large scattered light and the detected intensity of the forward small scattered light.

4 Claims, 16 Drawing Sheets

FOREIGN PATENT DOCUMENTS

| | | |
|---|---|---|
| JP | 3-12698 B2 | 2/1991 |
| JP | 3-24626 B2 | 4/1991 |
| JP | 5-43154 B2 | 6/1993 |
| JP | 8-50089 * | 2/1996 |
| JP | 8-50089 A | 2/1996 |
| JP | 8-20442 B2 | 3/1996 |
| JP | 8-128944 A | 5/1996 |
| JP | 2772370 B2 | 4/1998 |
| JP | 3350775 B2 | 9/2002 |

OTHER PUBLICATIONS

B.G. De Grooth, et al., "Light-Scattering Polarization Measurements as a New Parameter in Flow Cytometry", Cytometry 1987, Jun. 8, 1987, pp. 539-544.

R.M.P. Boornbos, et al., "White Blood Cell Differentiation Using a Solid State Flow Cytometer", Cytometry 1993, Mar. 16, 1993, pp. 589-594.

* cited by examiner

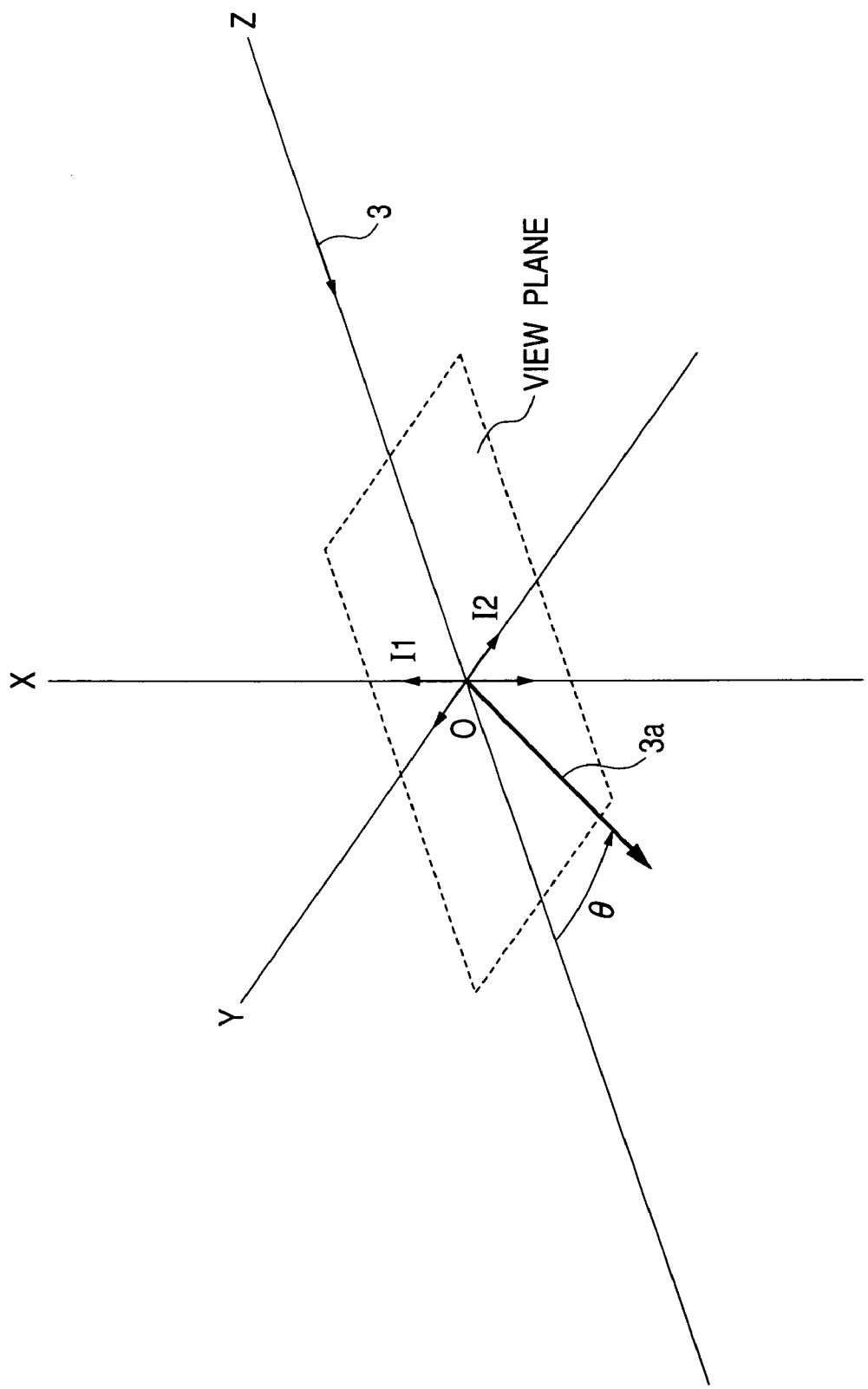

α=0.6

α=1.0

α=1.5

α=3.0

FLOW CYTOMETER FOR CLASSIFYING LEUKOCYTES AND METHOD FOR DETERMINING DETECTION ANGLE RANGE OF THE SAME

BACKGROUND OF THE INVENTION

The invention relates to a flow cytometer which classifies leukocytes by irradiating a blood sample, as well as to a method for determining a detection angle range of the flow cytometer.

Leukocyte cells comprise various blood cells, such as lymphocytes, monocytes, neutrophils, eosinophils, and basophils. Each of the cells consists of a nucleus and cytoplasm. The cells are known to differ in size and shape from each other, and particles included in cytoplasm, such as granules, are also known to differ in size, shape, and quantity from each other, depending on the type of cell. Granules or particles included in each cell have shown the following:

Lymphocyte: Very few granules of lymphocyte are present.
Monocyte: A considerably large number of granules, each having a granular size of 0.1 µm or less, are evenly present.
Neutrophil: A large number of glycogen granules ranging from 0.05 to 0.2 µm are present over a cell.
Eosinophil: A large number of special granules ranging from 0.5 to 1.0 µm are present.
Basophil: A large number of granules ranging from 0.2 to 1.0 µm are present.

These cells increase or decrease in number in accordance with a disease. Therefore, a disease is diagnosed by detecting the status of each cell on the basis of information about granules or particles in the cell. Therefore, classification of leukocytes is useful in clinical inspection.

In order to classify leukocytes with a flow cytometer, a blood sample including the leukocytes is irradiated by a laser beam originating from a laser light source so that the resultant scattered light, which differs in accordance with the type of a blood cell, is detected.

As disclosed in Japanese Patent No. 3350775 (corresponding to Japanese Patent Publication No. 8-271509A), the basic configuration of the flow cytometer is to classify leukocytes by making a sheath flow from a blood sample containing leukocytes, causing the sheath flow to pass through a tubule; irradiating a laser beam onto the flow of blood sample in the tubule orthogonally thereto; and detecting forward scattered light and orthogonal scattered light.

In U.S. Pat. No. 6,084,670, there is proposed adoption of a Fresnel lens as an optical lens to be used in the flow cytometer.

FIG. 1 shows the structure of a flow system and that of an optical detection system, both being located in the vicinity of a flow cell of the flow cytometer. These structures may be similarly applied to a flow cytometer of the invention.

A sample flow (i.e., a blood sample) $4b$ flows upward through a flow path formed in a quartz flow cell 4 while being sheathed in a sheath flow $4a$. In the sample flow $4b$, blood cells flow one after another in a line.

A laser beam 3 is emitted from a laser diode 1 to irradiate the sample flow $4b$ orthogonally thereto. When the particles flowing in the sample flow are exposed to the laser beam 3, optical scattering arises.

In relation to scattered light, a Fresnel lens $5a$ for detecting forward scattered light $3a$ and another Fresnel lens 8 for detecting orthogonal scattered light $3d$ are provided.

The Fresnel lens $5a$ is integrally constructed by arranging an inner ring-shaped Fresnel lens and an outer annular Fresnel lens in a concentric manner. A mask $5b$ is attached to a part of the Fresnel lens $5a$ facing the flow cell 4 such that the inner ring-shaped Fresnel lens receives forward small scattered light $3b$ and such that the outer annular Fresnel lens receives forward large scattered light $3c$. Here, an angle range in which detection is limited by the mask $5b$ corresponds to a scattering detection angle range outside the flow cell (described later).

Here, the intensity of the forward small scattered light correlates with the size of the particles (granules or nuclei) that have been exposed to the laser beam. The intensity of the forward large scattered light correlates with the complexity of the exposed particles. The intensity of the orthogonal scattered light correlates with granularity.

Here, the detection angle range of the scattered light at the outside of the flow cell will now be described by reference to FIGS. 4A and 4B.

As shown in FIG. 4A, the detection angle range at the outside of the flow cell is a range defined by representing, as a geometric (linear) angle, an area in which the Fresnel lens $5b$ detects scattered light while taking as a center a point of scattering at which blood cells in the sample flow $4a$ flowing through the flow cell 4 are irradiated by a laser beam.

Consequently, a range in which the forward small scattered light $3b$ is detected corresponds to a range defined between a1 and b1; a range in which the forward large scattered light $3c$ is detected corresponds to a range defined between c1 and d1; and a range in which the orthogonal scattered light $3d$ is detected corresponds to a range defined between e1 and f1.

In reality, as shown in FIG. 4B, the scattered light undergoes refraction at a boundary between the inside and outside of the flow cell 4 because of the refractive index of the flow cell 4, the refractive index of the sample flow $4b$ and the sheath flow $4a$ flowing through the flow cell 4, and a difference in refractive index between the inside and outside of the flow cell 4. Since the main component of each of the sheath flow $4a$ and the sample flow $4b$ is water, the refractive indices thereof are regarded as almost the same.

In view of the above, the scattering detection angle ranges within the flow cell will be considered.

FIG. 5 shows a range defined by the angle through which the laser beam radiated onto the sample flow in the flow cell 4 is scattered. The detection angle range of the forward small scattered light $3b$ corresponds to the range defined between a2 and b2. The detection angle range of the forward large scattered light $3c$ corresponds to the range defined between c2 and d2. The detection angle range of the orthogonal scattered light $3d$ corresponds to the range defined between e2 and f2.

A scattering angle outside of the flow cell and a scattering angle inside of the flow cell differ from each other depending on a refractive index of a liquid in the flow cell 4, a refractive index of the flow cell, and a refractive index of space (air) outside the flow cell. Further, a scattering angle outside of the flow cell and a scattering angle inside the flow cell differ from each other depending on the component and concentration of a reagent for processing blood required to produce a blood sample.

FIG. 2 is a block diagram showing the entire configuration of the flow cytometer.

The laser diode 1 radiates a laser beam 3 in accordance with a signal output from a laser diode controller 2 which has received a control signal from a processor 10. Forward scattered light $3a$ including forward small scattered light $3b$ and forward large scattered light 3c is divided by the mask 5b. Both light rays are collected by the Fresnel lens 5a and detected by detectors 6, 7.

Orthogonal scattered light 3d is collected by a Fresnel lens 8 and detected by a detector 9. The intensity of each of the scattered light rays detected by the detectors 6, 7, and 9 is transmitted to the processor 10. The processor 10 plots a distribution on a scattergram based on the detection signals, thereby classifying leukocytes.

The mask 5b is constructed as shown in FIG. 3. Reference numeral 3b' designates an area which enables passage of the forward small scattered light 3b, and 3c' designates an area which enables transmission of passage of the forward large scattered light 3c.

A cross pattern provided at the center of the mask 5b is provided for preventing detection of direct light of the laser beam 3 other than the light rays scattered by blood cells.

As mentioned above, there has been proposed a method of enhancing accuracy of classification of leukocytes, by detecting the forward scattered light which is divided into forward small scattered light and forward large scattered light.

Japanese Patent Publication No. 8-50089A also discloses the classification of leukocytes by detecting forward small scattered light and forward large scattered light. Specifically, scattered light falling within a region ranging from 1 to 5 degrees with respect to the optical axis of the incident light is detected as forward small scattered light, and scattered light falling within a region ranging from 6 to 20 degrees with respect to the optical axis of the incident light is detected as forward large scattered light. However, reasons why these regions are determined as detection angle ranges are not evident.

In addition to containing lymphocytes, monocytes, neutrophils, eosinophils, and basophils, blood sometimes contains immature leukocytes such as immature granulocytes including myeloblasts or myelocytes, or immature erythrocytes such as erythroblasts, all of which are usually present in bone marrow, but not in peripheral blood. Further, abnormal leukocytes, such as lymphoblasts, deformed lymphocytes, and abnormal lymphocytes, also sometimes emerge. Therefore, there is a necessity of identifying these immature or abnormal blood cells, thereby classifying leukocytes.

As has been known, an angle distribution of scattered light differs according to the size of particles when granules and particles are exposed to a laser beam. The light scattered by large particles substantially appear at a forward areas in a concentrated manner, and the intensity of the scattered light is proportional to the square of the diameter of a particle (according to Fraunhofer's diffraction theory). If particles have small diameters, the scattered light spreads in all directions, and the intensity of scattered light is proportional to the sixth power of the diameter of the corresponding particle (according to the Rayleigh's theory). The light scattered by small particles differs in angle distribution with respect to the oscillatory direction of incident light. As has also been known, if the particles have an irregular surface, a polarization phenomenon due to scattering does not arise.

When a laser beam having a wavelength $\lambda$ is radiated onto particles which are included in leukocyte cells and have a diameter "d," a particle parameter can be expressed as:

$$\alpha = \pi d/\lambda \quad (1)$$

given that the particle parameter is defined as $\alpha$.

The angle distribution of scattered light intensity can be expressed as shown in FIG. 13 according to the oscillatory direction of incident light. It is assumed that linearly-polarized incident light (i.e., a laser beam 3) enters along the Z axis and is scattered by a particle of leukocyte cell placed at the point of origin, in the direction of $\theta$ (scattering angle) with respect to the Z axis (here, the scattered light is represented by an arrow 3a). A plane parallel to Y-Z plane is taken as a view plane. The incident light is assumed such that an oscillatory direction of an electric field is linearly polarized in parallel with X-Z plane, and an oscillatory direction of a magnetic field is linearly polarized in parallel with the view plane (i.e., Y-Z plane).

Scattered light intensity is obtained from the light scattered by the particle along oscillatory planes. Here, the intensity of scattered light having a component perpendicular to the view plane (i.e., X-Z plane) is taken as I1, and the intensity of scattered light having a component parallel to the view plane (i.e., Y-X plane) is taken as I2. According to the Mie's scattering theory, the intensity of scattered light can be calculated by the following equation.

$$I = \int_{\omega c} \frac{F(\theta, \psi, \alpha, m)}{K2R2} I i d\omega \quad (2)$$

where $\alpha = \pi d_p/\lambda$
$K = 2\pi/\lambda$
I: intensity of scattered light
Ii: intensity of incident light (hereinafter called "incident light intensity")
$\lambda$: wavelength
$d_p$: particle size ("p" means particle)
$\omega_c$: light focusing solid angle
m: relative refractive index between a medium and a particle
R: distance from a particle to an observation point
$\theta, \psi$: incoming and outgoing directions of light in a spherical coordinate system As shown in FIGS. 14A and 14B, the thus-computed scattered light intensities I1 and I2 shows distributions on the basis of the scattering angle $\theta$ of the particle. Since the scattered light intensity I1 changes according to an angle at an electric field oscillation plane, it is obtained a distribution in the form of a pair of eyeglasses, such as that shown in FIG. 14A. The scattered light intensity I2 is identical at any angle on a magnetic field oscillation plane. Hence, it is obtained a distribution in the form of a circle such as that shown in FIG. 14B.

In a case where the incident light is not linearly polarized, the scattered light intensities I1 and I2 are added, whereby a merged distribution such as that shown in FIG. 14C is obtained. The distribution pattern of merged scattered light intensities changes according to the value of the particle size parameter $\alpha$ of Equation 1. The left side of the coordinate system with respect to the center in FIG. 14C shows a pattern of a forward scattered light component, and upper and lower patterns show patterns of an orthogonal scattered light component. The right side of the coordinate system with respect to the center shows a pattern of backward scattered light components. When the particle size parameter $\alpha$ is 0 or very small, a laterally-symmetric pattern as illustrated is obtained. Further, all these patterns are vertically symmetric.

FIGS. 15A to 15D show changes in particle size parameter $\alpha$; that is, changes in the sizes of particles in a cell, wherein FIG. 15A shows a pattern for a particle size parameter α=0.6;

FIG. 15B shows a pattern for a particle size parameter α=1.0;

FIG. 15C shows a pattern for a particle size parameter α=1.5; and

FIG. 15D shows a pattern for a particle size parameter α=3.0.

As is evident from these figures, a backward scattered light component becomes smaller as the particle size parameter α increases; that is, as a particle becomes larger. On the other hand, a forward scattered light component extends in the direction of the incident light axis as a particle becomes larger.

A scattergram employing the intensity of detected forward small scattered light and the intensity of detected forward large scattered light as axes is defined as a scattergram denoted by SC1 shown in FIG. 16. In the scattergram SC1, the respective reference characters represent as follows:

|  |  |
|---|---|
| Ne: | neutrophil |
| Ly: | lymphocyte |
| Mo: | monocyte |
| Eo: | eosinophil |
| Ba: | basophil |

In order to separate and analyze the monocytes, the basophils, and the lymphocytes in more detail, a scattergram SC2 is prepared based on the forward small scattered light intensity range in the scattergram SC1 where monocytes, basophils, and lymphocytes are distributed and an appropriate orthogonal scattered light intensity range.

In order to separate and analyze the neutrophils and the eosinophils in more detail, a scattergram SC3 is prepared based on the forward small scattered light intensity range in the scattergram SC1 where neutrophils and eosinophils are distributed and an appropriate orthogonal scattered light intensity range.

In the related-art flow cytometer, with respect to the irradiating direction of laser beam 3, the range in which the forward small scattered light 3b is to be detected, the range in which the forward large scattered light 3c is to be detected, and the range in which the orthogonal light 3d is to be detected are determined as shown in Table 1. It is adopted a reagent sodium polyoxyethylene 3 alkyle ($C_{12}$–$C_{13}$ mixture) ether sulfate [i.e., a reagent using a chemical formula $C_{12\text{-}13}$—O—$(CH_2CH_2O)_3$—$SO_3Na$] which serves as a hemolytic agent compound and is a kind of polyoxyethylene anionic active agent is disclosed as EXAMPLE 1 (a hemolytic agent component) in U.S. Pat. No. 5,747,343.

TABLE 1

|  | for forward small scattered light | for forward large scattered light | for orthogonal scattered light |
|---|---|---|---|
| detection angle range outside flow cell | 0.9–5.0 (degrees) | 10–16 (degrees) | 63–117 (degrees) |
| detection angle range inside flow cell | 0.7–3.9 (degrees) | 8–12 (degrees) | 69–111 (degrees) |

The "detection angle range outside the flow cell" provided in an upper row of Table 1 is a range defined by representing, as a geometric (linear) angle, an area in which the Fresnel lens 5b detects scattered light while taking as a center a point of scattering at which the blood cells in the sample flow 4b is irradiated by the laser beam 3 (see FIG. 4A).

The "detection angle range inside the flow cell" provided in a lower row of Table 1 is a range in which the Fresnel lens 5b actually detects scattered light while taking as a center a point of scattering at which the blood cells in the sample flow 4b is irradiated by the laser beam 3 (see FIGS. 4B and 5).

Therefore, the scattered light detection angle range outside the flow cell may slightly deviate from the scattered light detection angle range inside the flow cell, depending on a refractive index of the flow cell 4, a refractive index of the interior or exterior of the flow cell 4, and the design dimensions of the flow cell 4.

The scattergram obtained by the configurations shown in Table 1 will be described layer. Here, substantially the same result can be obtained through use of a reagent disclosed as EXAMPLE 2 (a hemolytic agent component) in U.S. Pat. No. 5,747,343, wherein a reagent sodium polyoxyethylene 3 alkyle ($C_{11}$–$C_{15}$ mixture) ether sulfate serves as a hemolytic agent compound and is a kind of polyoxyethylene anionic active agent.

However, in the scattergram plotted with the intensity of the forward large scattered light and the intensity of the forward small scattered light are taken as axes, lymphocytes and monocytes are distributed in close proximity to each other. If these distributions are separated from each other, accurate measurement can be performed.

Since the neutrophils and eosinophils are in close proximity to each other on the scattergram, accurate measurement can be performed, so long as the distributions can be separated from each other.

When large immature cells have arisen, the distribution of the neutrophils and a distribution of the large immature cells are close to each other on the scattergram using the intensity of the forward large scattered light and the intensity of the forward small scattered light as axes. Hence, confusion of measurement may arise between these two types of cells.

SUMMARY OF THE INVENTION

It is therefore an object of the invention to improve distinction of monocytes from lymphocytes, distinction of neutrophils from eosinophils, and distinction of large immature cells from neutrophils.

In order to achieve the above object, according to the invention, there is provided a flow cytometer, comprising:

a flow cell, through which a blood sample containing leukocytes flows;

a light source, which emits a light beam in a first direction, the light beam to be incident into the flow cell and scattered by the blood sample as scattered light;

a first detector, which detects an intensity of forward small scattered light out of the scattered light, the first detector arranged so as to have a maximum angle of a detection angle range for the forward small scattered light stemmed from the first direction at a position outside of the flow cell, which is 4 degrees or less (or 3.1 degrees at a position inside of the flow cell);

a second detector, which detects an intensity of forward large scattered light out of the scattered light, the second detector arranged so as to have a detection angle range for the forward large scattered light stemmed from the first direction at a position outside of the flow cell, which falls in a range from 10 degrees to 16 degrees (or 8 degrees to 12 degrees at a position inside of the flow cell); and a processor, which classifies the leukocytes based on the detected intensity of the forward large scattered light and the detected intensity of the forward small scattered light.

This means that the first detector is arranged so as to have a maximum angle of a detection angle range for the forward small scattered light stemmed from the first direction, such that a lowest intensity of the forward small scattered light among intensities of the forward small scattered light scattered by the monocytes contained in the blood sample is sufficiently greater than a highest intensity of the forward small scattered light among intensities of the forward small scattered light scattered by the lymphocytes contained in the blood sample.

In order to surely classify the monocytes and the lymphocytes, this further means that the first detector is arranged so as to have a maximum angle of a detection angle range for the forward small scattered light stemmed from the first direction, which is sufficiently inner than a portion at which an intensity change of the forward small scattered light according to Fraunhofer's diffraction (derived from monocytes contained in the blood sample) per unit scattering angle becomes largest.

In order to surely classify neutrophils and eosinophils, the first detector may be arranged so as to have a maximum angle of a detection angle range for the forward small scattered light stemmed from the first direction, such that a lowest intensity of the forward small scattered light among intensities of the forward small scattered light scattered by the neutrophils contained in the blood sample is sufficiently greater than a highest intensity of the forward small scattered light among intensities of the forward small scattered light scattered by the eosinophils contained in the blood sample.

Similarly, the first detector may be arranged so as to have a maximum angle of a detection angle range for the forward small scattered light stemmed from the first direction, which is sufficiently inner than a portion at which an intensity change of the forward small scattered light according to Fraunhofer's diffraction (derived from neutrophils contained in the blood sample) per unit scattering angle becomes largest.

In order to surely classify neutrophils and large immature cells, the first detector may be arranged so as to have a maximum angle of a detection angle range for the forward small scattered light stemmed from the first direction, such that an intensity distribution of the forward small scattered light derived from neutrophils contained in the blood sample is distinguishably separated from an intensity distribution of the forward small scattered light derived from large immature cells contained in the blood sample.

Similarly, the first detector may be arranged so as to have a maximum angle of a detection angle range for the forward small scattered light stemmed from the first direction, which is sufficiently inner than a portion at which an intensity change of the forward small scattered light according to Fraunhofer's diffraction (derived from large immature cells contained in the blood sample) per unit scattering angle becomes largest.

According to the invention, there is also provided a method of determining a detection angle range for scattered light in a flow cytometer, comprising steps of:
   setting one detection angle range;
   detecting light scattered by a sample containing a plurality of kinds of particles or cells with the set detection angle range;
   estimating an intensity distribution of the detected scattered light with respect to each kind of the particles or cells; and
   optimizing the detection angle range based on differences among estimated distributions of the respective kinds of particles or cells.

According to the invention, there is also provided a flow cytometer, having a detection angle range for scattered light determined by the above method.

BRIEF DESCRIPTION OF THE DRAWINGS

The above objects and advantages of the present invention will become more apparent by describing in detail preferred exemplary embodiments thereof with reference to the accompanying drawings, wherein:

FIGS. 13 through 14C are diagrams for explaining the intensity distribution of the scattered light resulting from an angular difference in oscillatory direction of incident light;

DETAILED DESCRIPTION OF THE PREFERRED EMBODIMENTS

Figure 1:
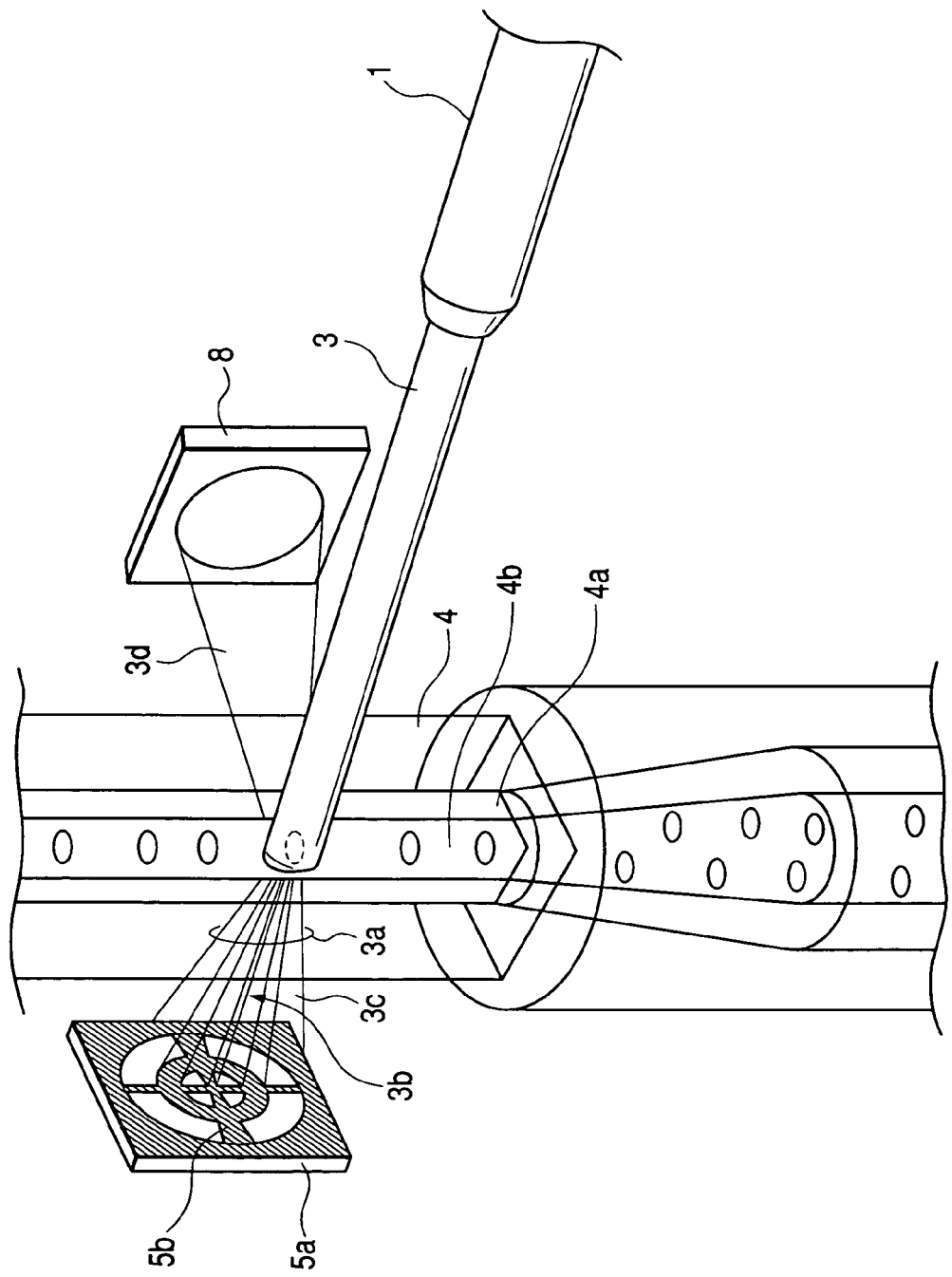
FIG. 1 is a schematic perspective view showing an essential portion of a flow cytometer.
Figure 2:
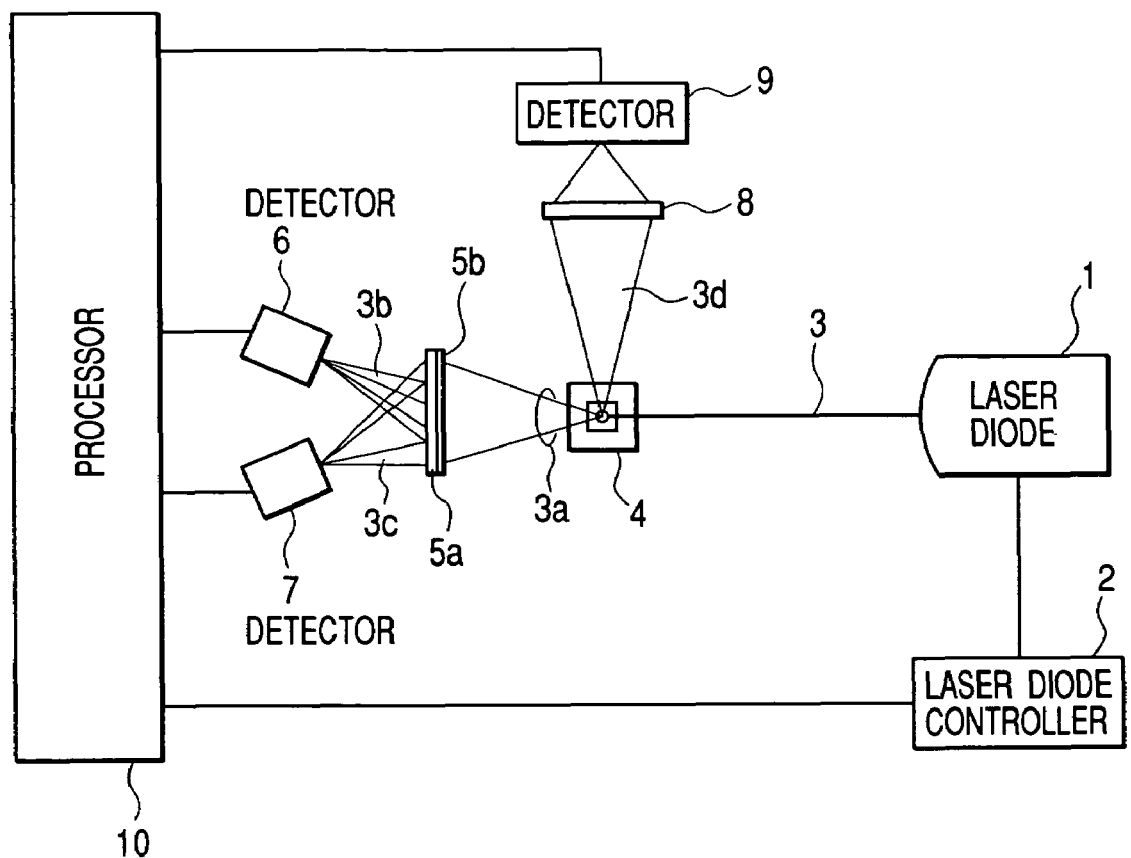
FIG. 2 is a block diagram showing the entire configuration of the flow cytometer.
Figure 3:
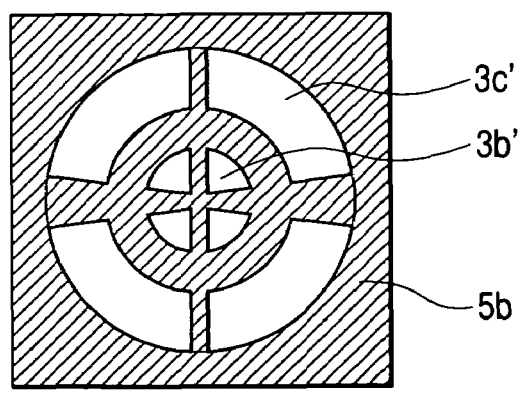
FIG. 3 is a plan view showing a mask provided in the flow cytometer.

The structure of a flow system and that of an optical detection system, both being located in the vicinity of a flow cell of a flow cytometer of the invention, are the same as those shown in FIG. 1 . The entire configuration of the flow cytometer of the invention is identical with that shown in FIG. 2. A cross section of a flow path provided in a quartz flow cell 4 (4.2 mm×4.2 mm) assume a size of 250 μm×250 μm.

Figure 4A:
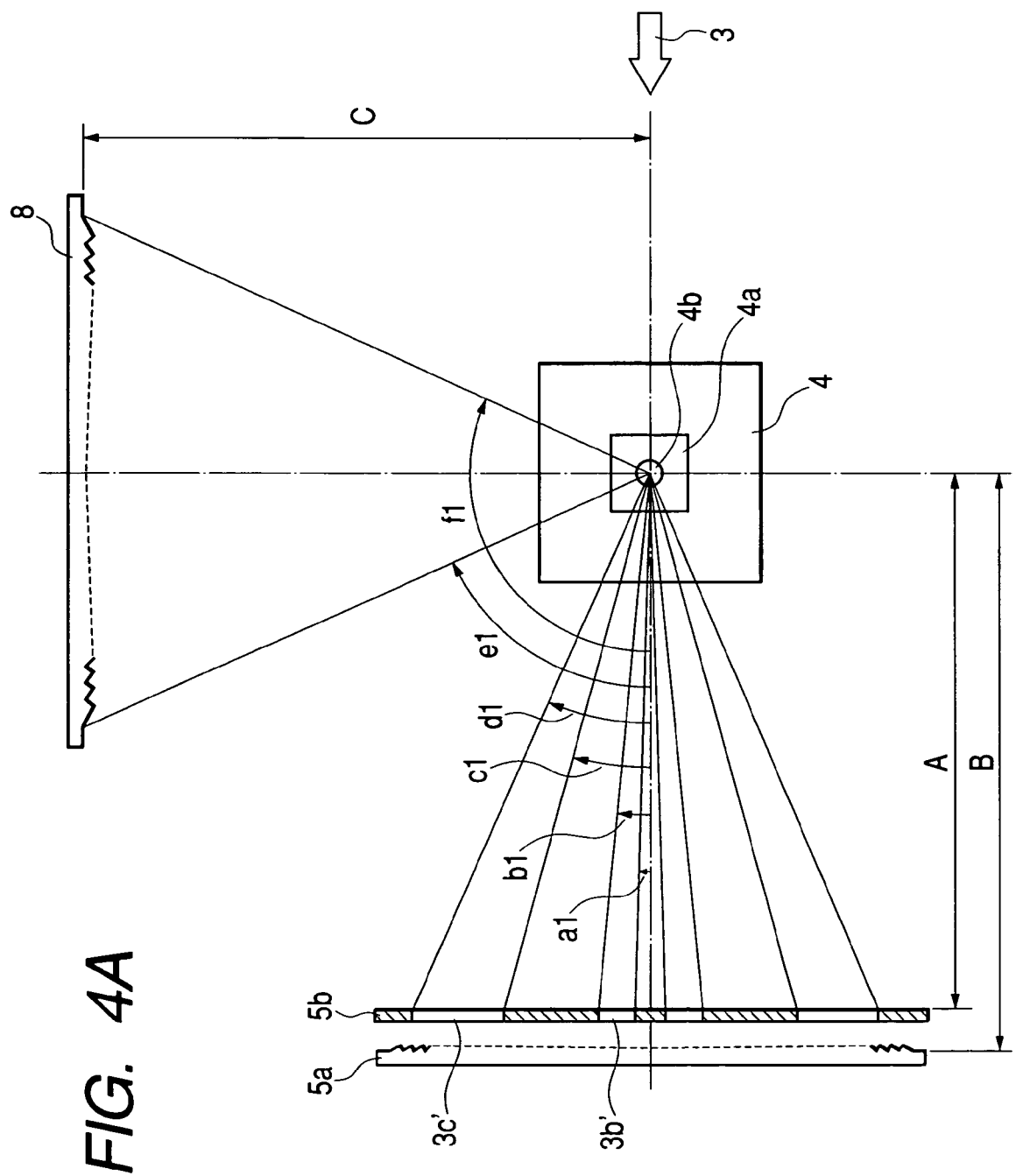
FIG. 4A is a view for describing a scattering angle range outside a flow cell.
Figure 4B:
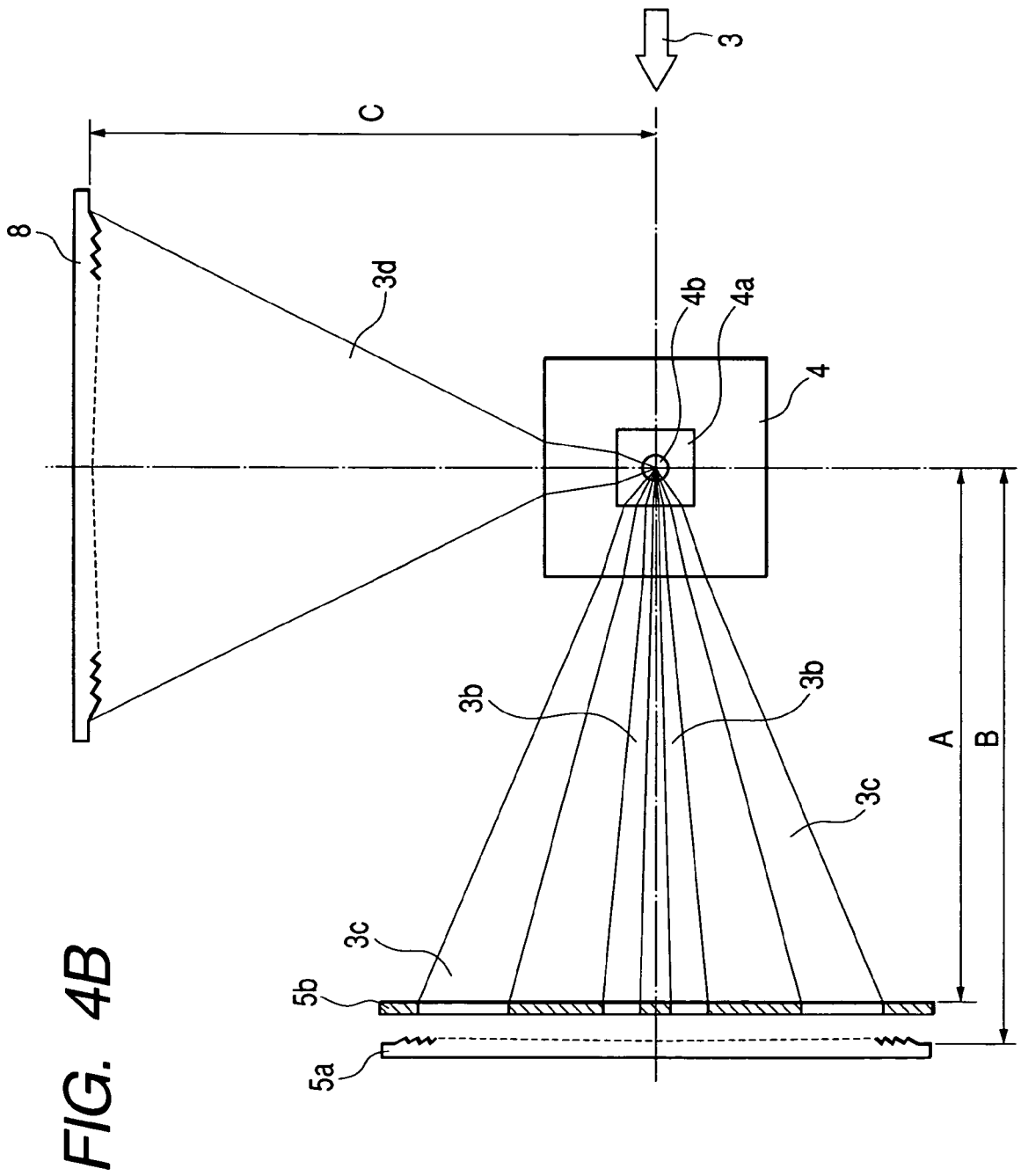
FIG. 4B is a view showing a scattering phenomenon arising outside and inside the flow cell.
Figure 5:
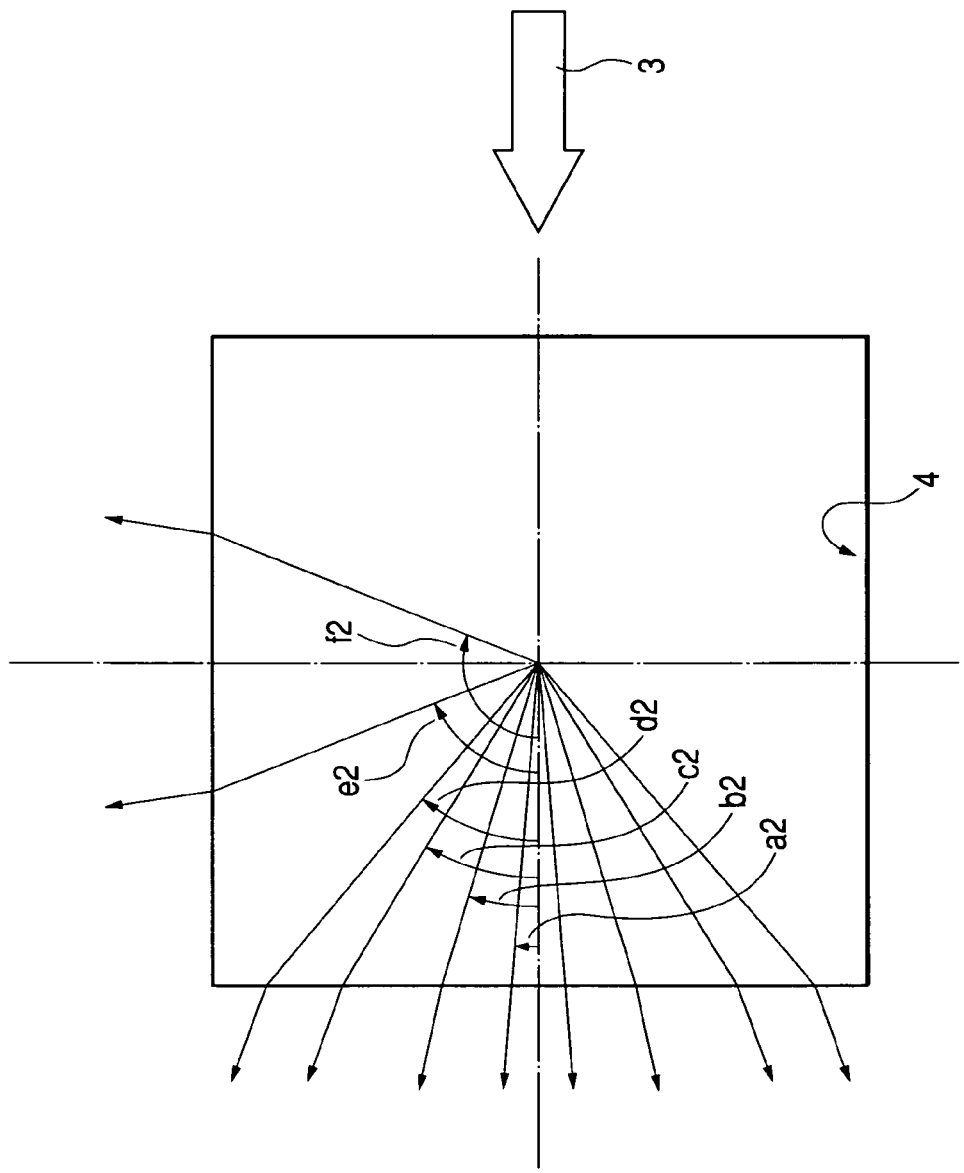
FIG. 5 is a view for describing the scattering angle range inside the flow cell.

For information about the scattered light detection angle range inside and outside the flow cell 4, please refer to FIGS. 4A, 4B, and 5 and associated explanations. A distance A from the sectional center of the flow path of the flow cell 4 to a mask 5b is 32.4 mm; a distance B from the sectional center of the flow path of the flow cell 4 to a Fresnel lens 5a for detecting forward scattered light is 33 mm; and a distance C from the sectional center of the flow path of the flow cell 4 to a Fresnel lens 8 for detecting orthogonal scattered light is 33 mm. These distances can be set as required.

Similar to the related-art flow cytometer, the reagent employed for measurement is EXAMPLE 1 selected from among the reagents described in U.S. Pat. No. 5,747,343. A substantially similar result is yielded even when EXAMPLE 2 disclosed in the same patent is used.

The inventors performed measurement while changing a range for detecting forward small scattered light, and consequently obtained interesting results. Data pertaining to the detection angle range provided in Table 2 will be described as a typical result in comparison with the data provided in Table 1 (i.e., a detection angle range adopted in the related-art flow cytometer).

TABLE 2

| | for forward small scattered light | for forward large scattered light | for orthogonal scattered light |
|---|---|---|---|
| detection angle range outside flow cell | 0.9–4.0 (degrees) | 10–16 (degrees) | 63–117 (degrees) |
| detection angle range inside flow cell | 0.7–3.1 (degrees) | 8–12 (degrees) | 69–111 (degrees) |

Figure 6:
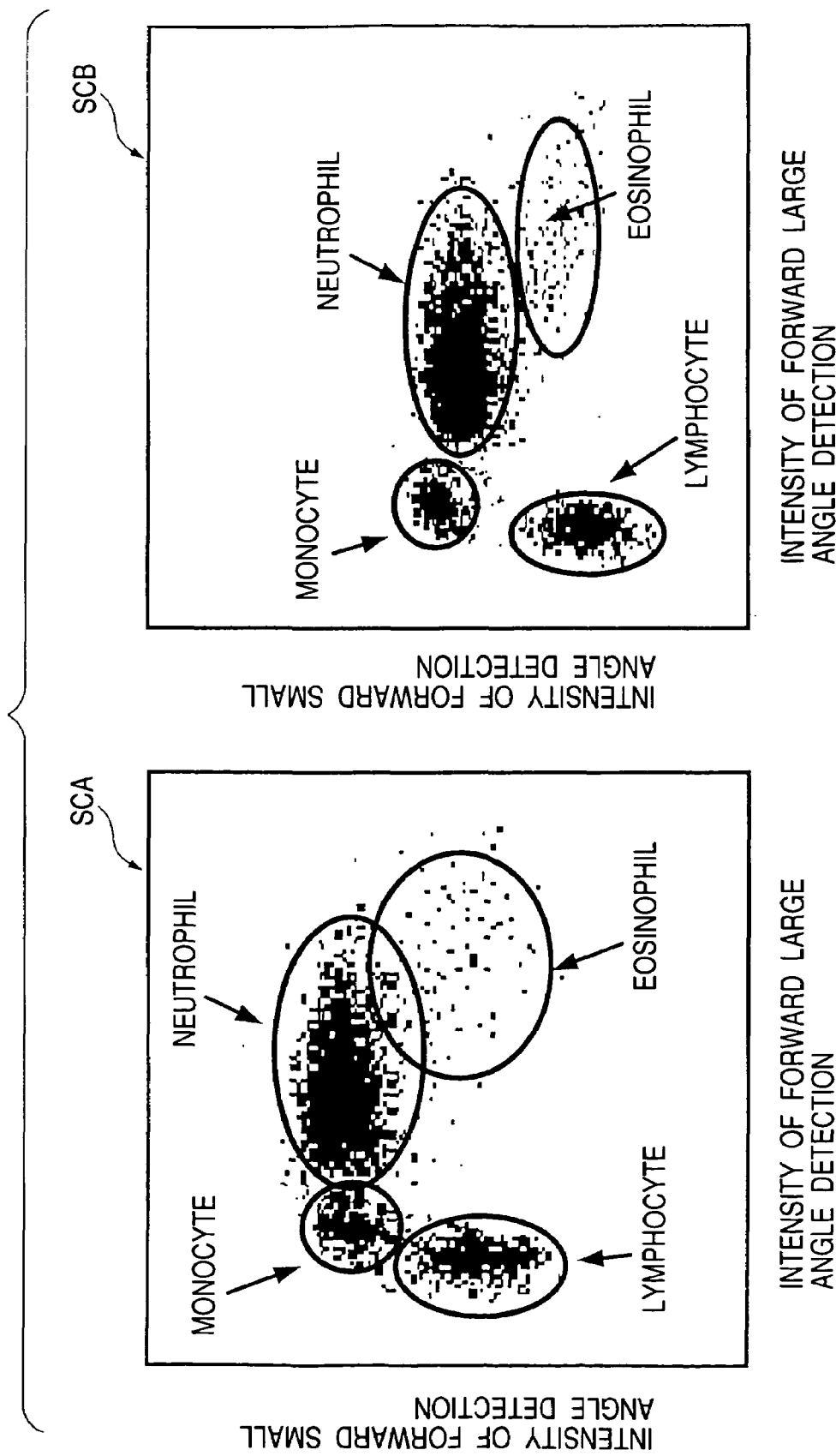
FIG. 6 shows scattergrams defined by taking a normal blood as a sample while the intensity of the forward small scattered light and the intensity of the forward large scattered light are taken as axes, before and after improvement of a detection angle for the forward small scattering light.

FIG. 6 show scattergrams which pertain to a single normal blood sample and are plotted as scattergrams with the intensity of forward large scattered light being taken as a horizontal axis and the intensity of forward small scattered light being taken as a vertical axis. Lymphocytes, monocytes, neutrophils, and eosinophils are distributed.

The scattergram SCA shows the data obtained within the scattered light detection angle range of Table 1.

The scattergram SCB shows the data obtained within the scattered light detection angle range of Table 2.

A comparison between the scattergrams SCA and SCB reveals that the intensity of forward small scattered light becomes weak as a result of the range for detecting forward small scattered light having been narrowed.

The comparison also reveals that the distribution of lymphocytes and the distribution of monocytes, which are close to each other in the scattergram SCA, have become separated from each other in the scattergram SCB, thus improving the accuracy of classification.

The comparison further reveals that the distribution of neutrophils and the distribution of eosinophils, which are close to each other in the scattergram SCA, are concentrated into smaller areas as shown in the scattergram SCR, thereby improving the accuracy of classification.

Figure 7:
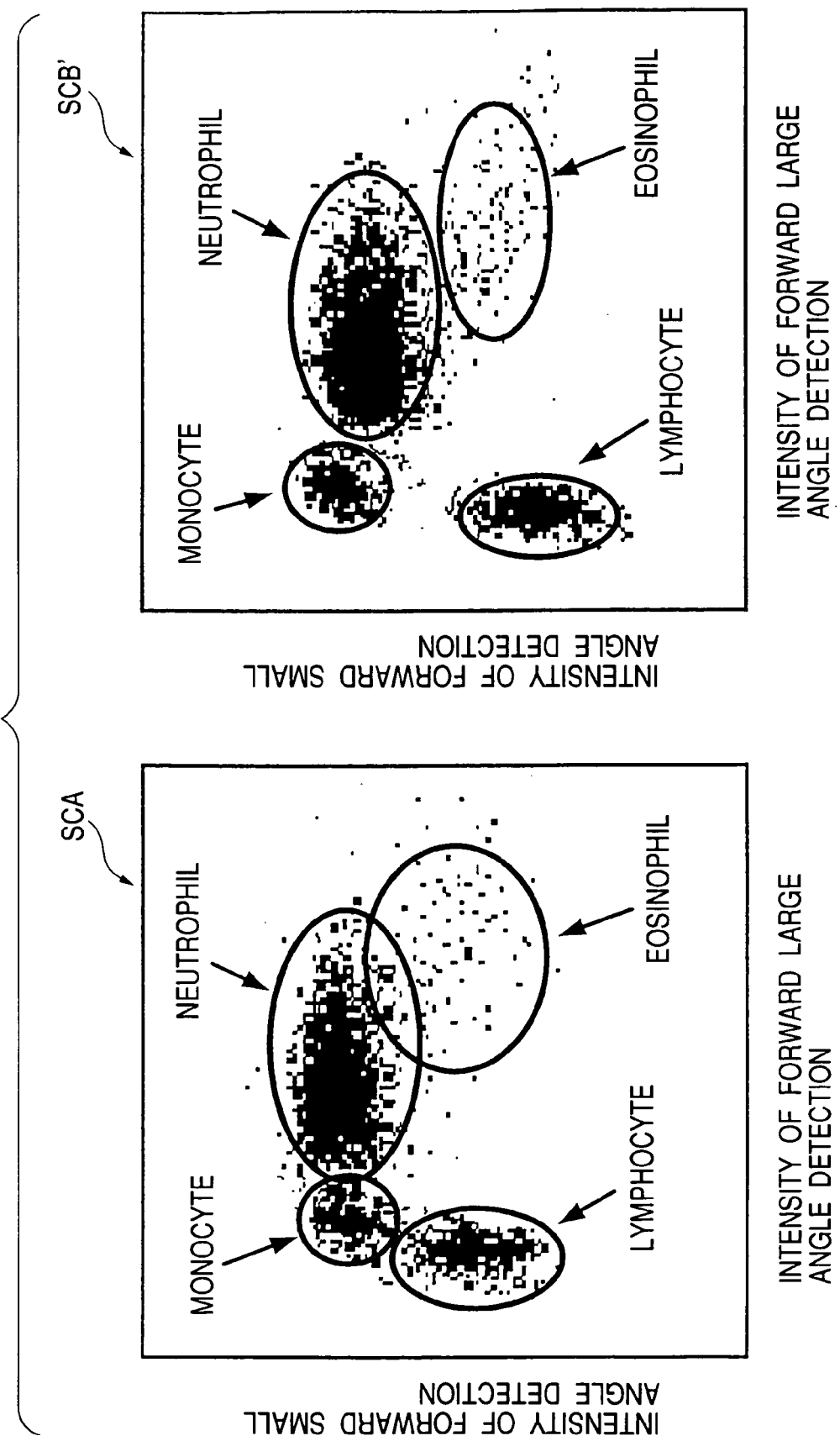
FIG. 7 shows scattergrams analogous to that shown in FIG. 6, wherein the scattergram is corrected while monocytes are taken as a reference with respect to the axis of intensity of forward small scattered light.

In FIG. 7, a scattergram SCB' is obtained by correcting the data shown in the scattergram SCB. Specifically, the data in the scattergram SCB are multiplied by a constant magnification with respect to the vertical axis, such that the barycenter of distribution of monocytes becomes identical in position with that shown in the scattergram SCA. It is understood that the correction made in the scattergram SCB' renders noticeable separation between the distribution of lymphocytes and the distribution of monocytes. Similarly, the correction is also understood to render noticeable separation between the distribution of neutrophils and the distribution of eosinophils.

Figure 8:
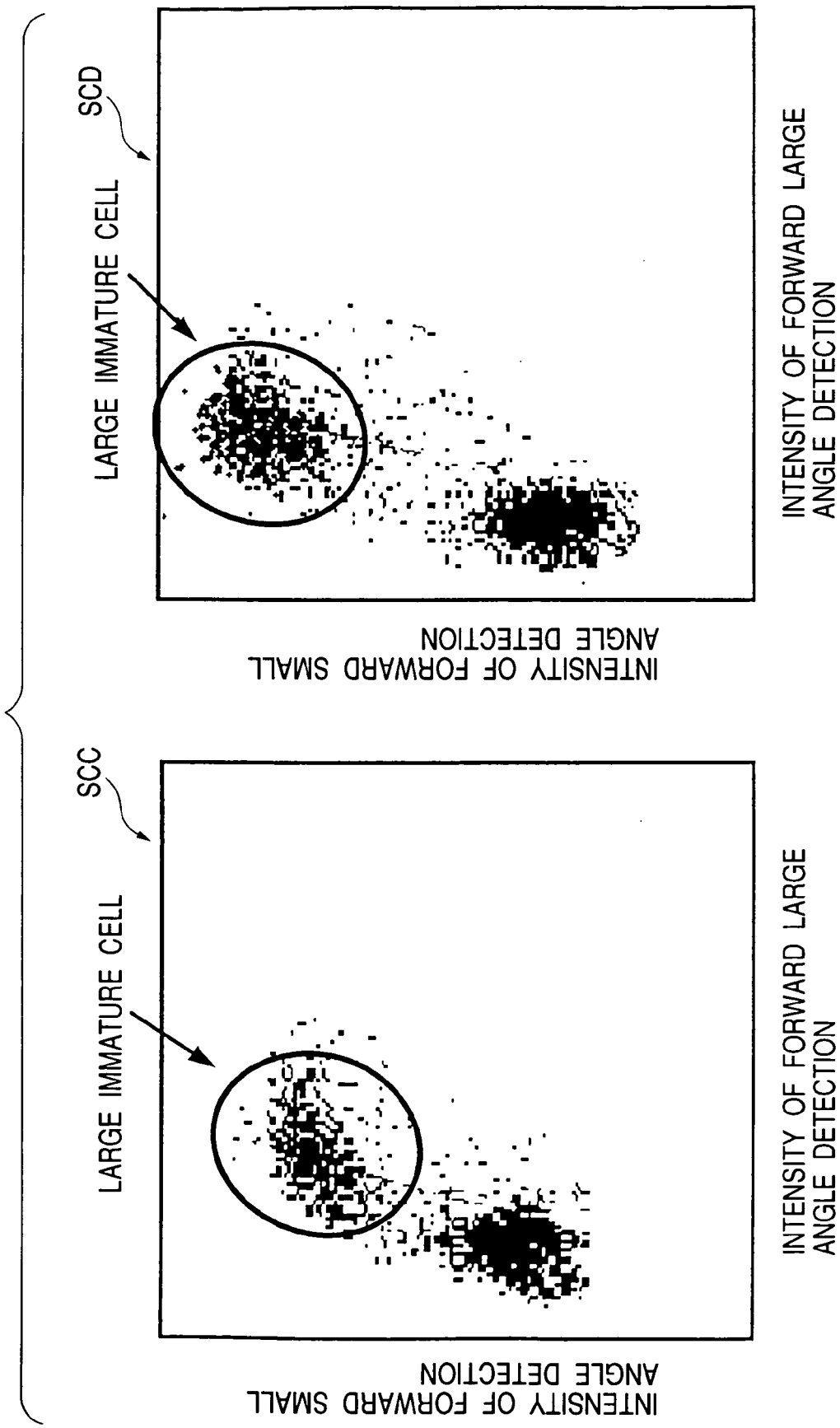
FIG. 8 shows scattergrams pertaining to a blood sample including large immature cells with the intensity of forward small scattered light and the intensity of forward large scattered light being taken as axes, before and after improvement of the detection angle for the forward small scattered light.

FIG. 8 shows scattergrams SCC and SCD pertaining to the same blood sample which includes large immature cells and is plotted with the intensity of forward large scattered light being taken as the horizontal axis and the intensity of forward small scattered light being taken as the vertical axis. In the drawing, encircled areas designate the distribution of the large immature cells.

The large immature cells include immature granulocytes such as myeloblasts and sometimes include immature cells other than granulocytes.

The scattergram SCC shows data obtained within the scattered light detection angle range of Table 1.

The scattergram SCD shows data corrected by multiplying data obtained within the scattered light detection angle range of Table 2 by a constant magnification with respect to the vertical axis, such that the barycenter of distribution of monocytes becomes identical in position with that in the scattergram SCC.

It is understood that the distribution of monocytes and the distribution of large immature cells, which are close to each other in the scattergram SCC, are separated from each other in the scattergram SCD, thus improving the accuracy of classification.

Figure 9:
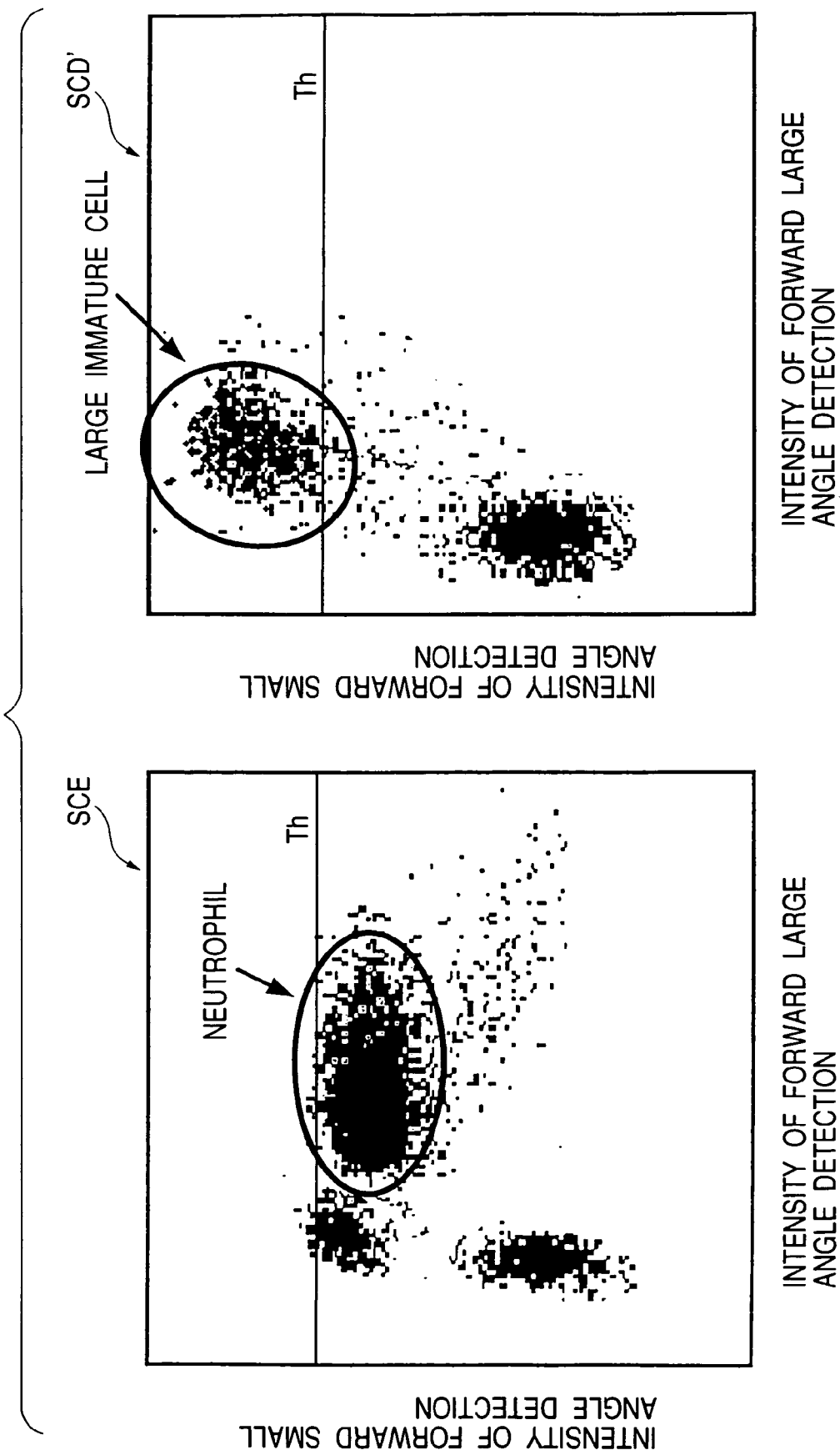
FIG. 9 shows scattergrams pertaining to a blood sample including large immature cells with the intensity of forward small scattered light and the intensity of forward large scattered light being taken as axes, showing distributions of neutrophils and large immature cells.

In FIG. 9, a scattergram SCE shows data pertaining to neutrophils in the normal blood sample and obtained within the scattered light detection angle range of Table 2. A scattergram SCD' shows the same distribution shown in the scattergram SCD but a threshold line Th (described later) is added. Similarly, the intensity of forward large scattered light being taken as the horizontal axis and the intensity of forward small scattered light being taken as the vertical axis. A threshold line Th shown in the scattergram SCE designates the same level as that in the scattergram SCD' in connection with the vertical axis.

As can be seen from comparison between the scattergrams SCE and SCD', the distribution of neutrophils in the normal blood sample is separated from the distribution of large immature cells in the blood sample including large immature cells, with reference to the threshold line Th. Thus, the neutrophils and the large immature cells have become more easy to classify.

Figure 10:
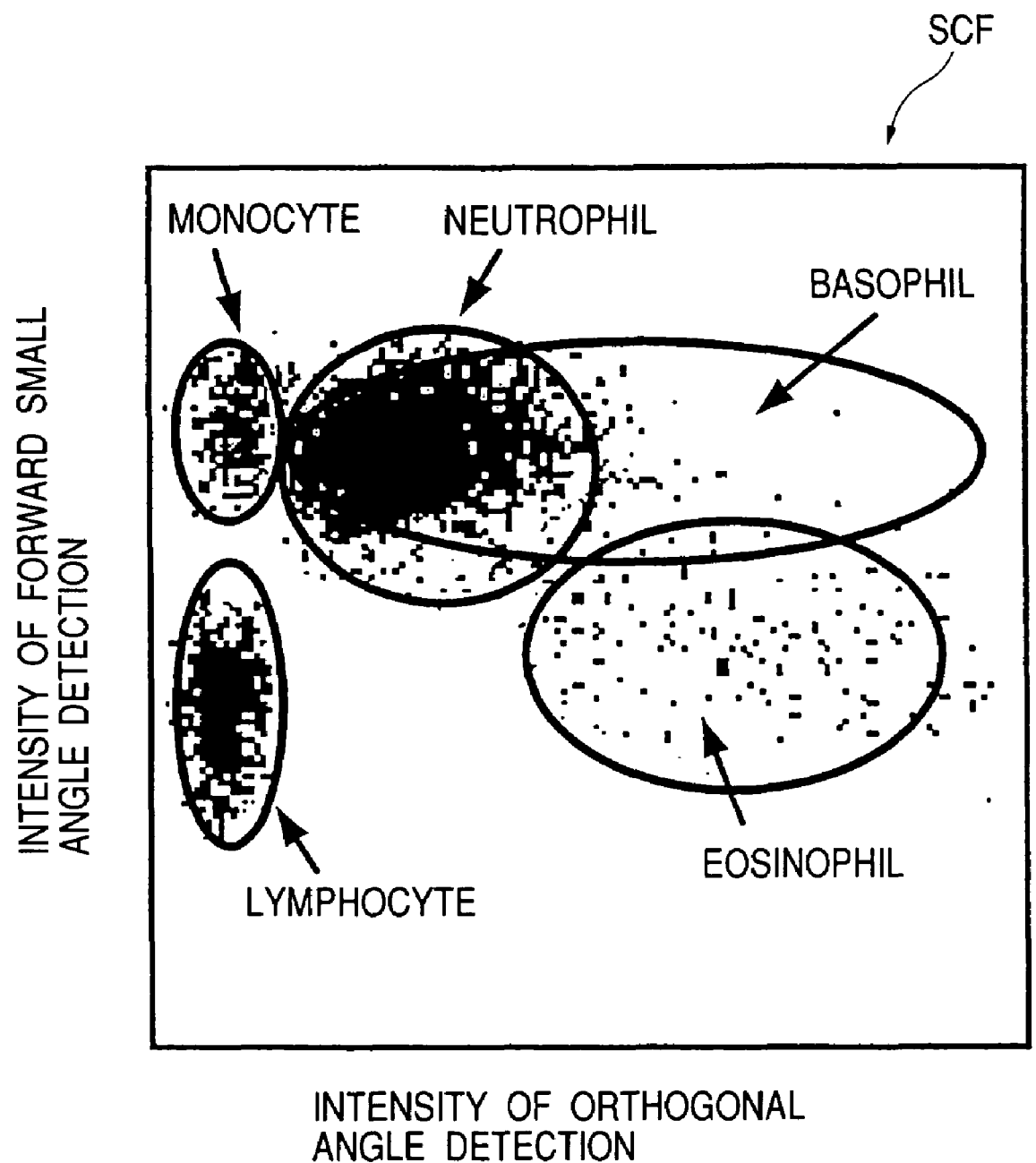
FIG. 10 is a scattergram pertaining to a normal blood sample with the intensity of forward small scattered light and the intensity of orthogonal scattered light being taken as axes.

FIG. 10 shows data which are plotted in the form of a scattergram with the intensity of orthogonal scattered light being taken as the horizontal axis and the intensity of forward small scattered light being taken as the vertical axis. The scattergram SCF shows the distribution of monocytes, that of neutrophils, that of eosinophils, and that of basophils. This scattergram shows a relationship between the intensity level of the orthogonal scattered light and the intensity level of the forward small scattered light.

There will be described estimation of distributions of light scattered by various leukocytes based on the intensities of the scattered light.

The distributions are estimated on the basis of the intensity of detected forward small scattered light, the intensity of detected forward large scattered light, and the intensity of detected orthogonal scattered light without considering extremums of the respective scattered light distributions.

Although individual differences are included, a relationship between the intensity levels of light scattered by various leukocytes is summarized as shown in Table 3.

TABLE 3

| | relationship between intensity levels |
|---|---|
| forward small scattered light | LIC > MO, MO ≈ NE > LY |
| forward large scattered light | EO > NE > LIC > MO > LY |
| orthogonal scattered light | NE > LIC, MO, LY |

Here,
NE: Neutrophils
LY: Lymphocytes
MO: Monocytes
EO: Eosinophils
Ba: Basophils
LIC: Large immature cells As a result of the forward small scattered light detection angle range being made narrow without involvement of a change to the forward large scattered light detection angle range (i.e., a change from the conditions provided in Table 1 to those provided in Table 2), the intensity of forward large scattered light remains substantially intact as shown in FIG. 6, whereby the overall intensity of the forward small scattered light has become low.

As mentioned above, light scattering differs in accordance with the size of granules or particles included in blood cells. Fraunhofer's diffraction theory states that if the particles are of large size in diameter, scattered light is concentrated at a forward area. Meanwhile, Rayleigh's scattering theory states that when the particles are of small size in diameter, such as granules, light is spread in all directions. In this case, light scattering according to the Mie's scattering theory is also taken into consideration.

Therefore, the distribution of light scattered by blood cells is created as a result of an overlap between Fraunhofer's diffraction, Rayleigh's scattering, and Mie's scattering of the various granules and various particles existing in the blood cells.

Figure 11:
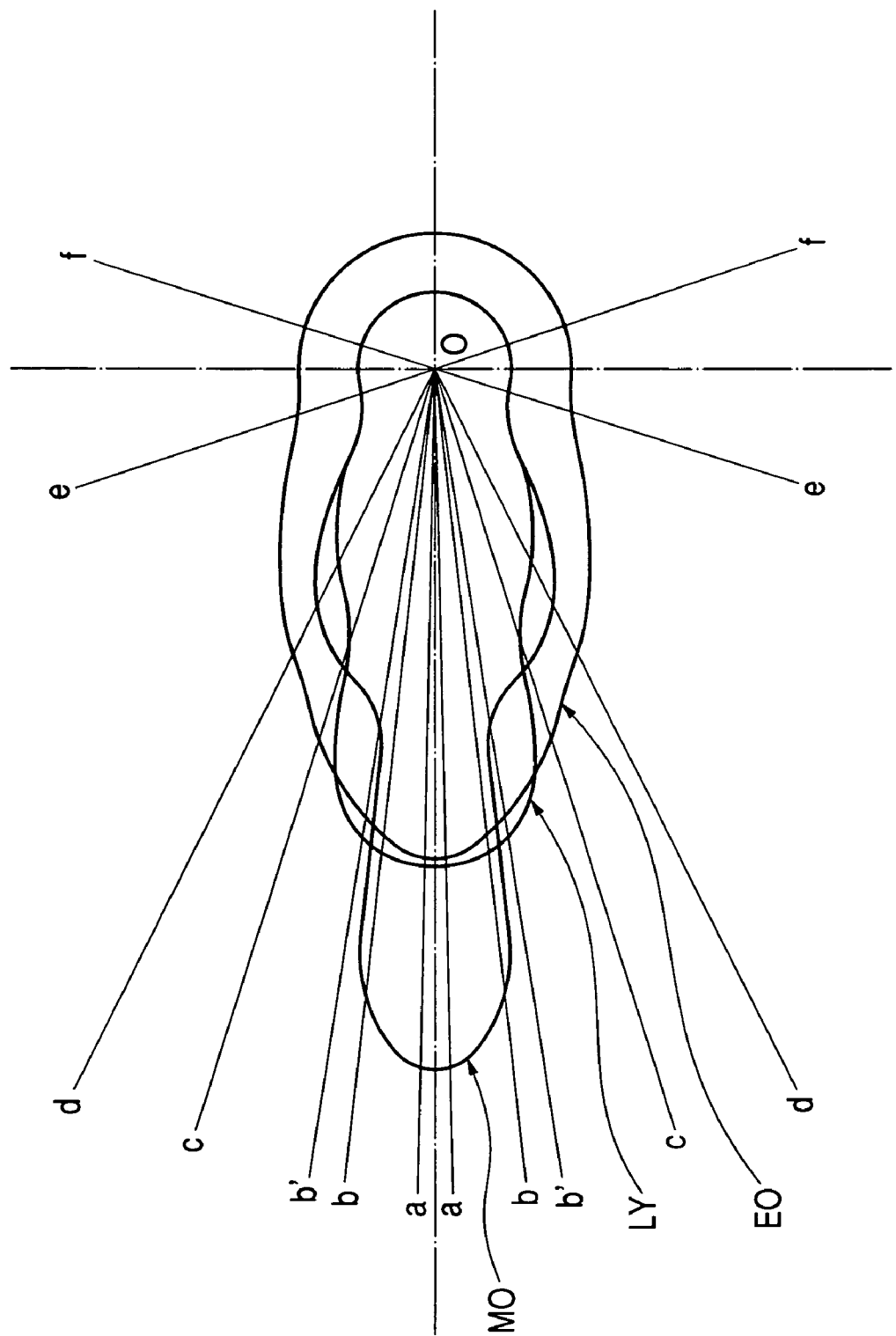
FIG. 11 shows estimated distribution of light scattered by monocytes, lymphocytes, and eosinophils.
Figure 12:
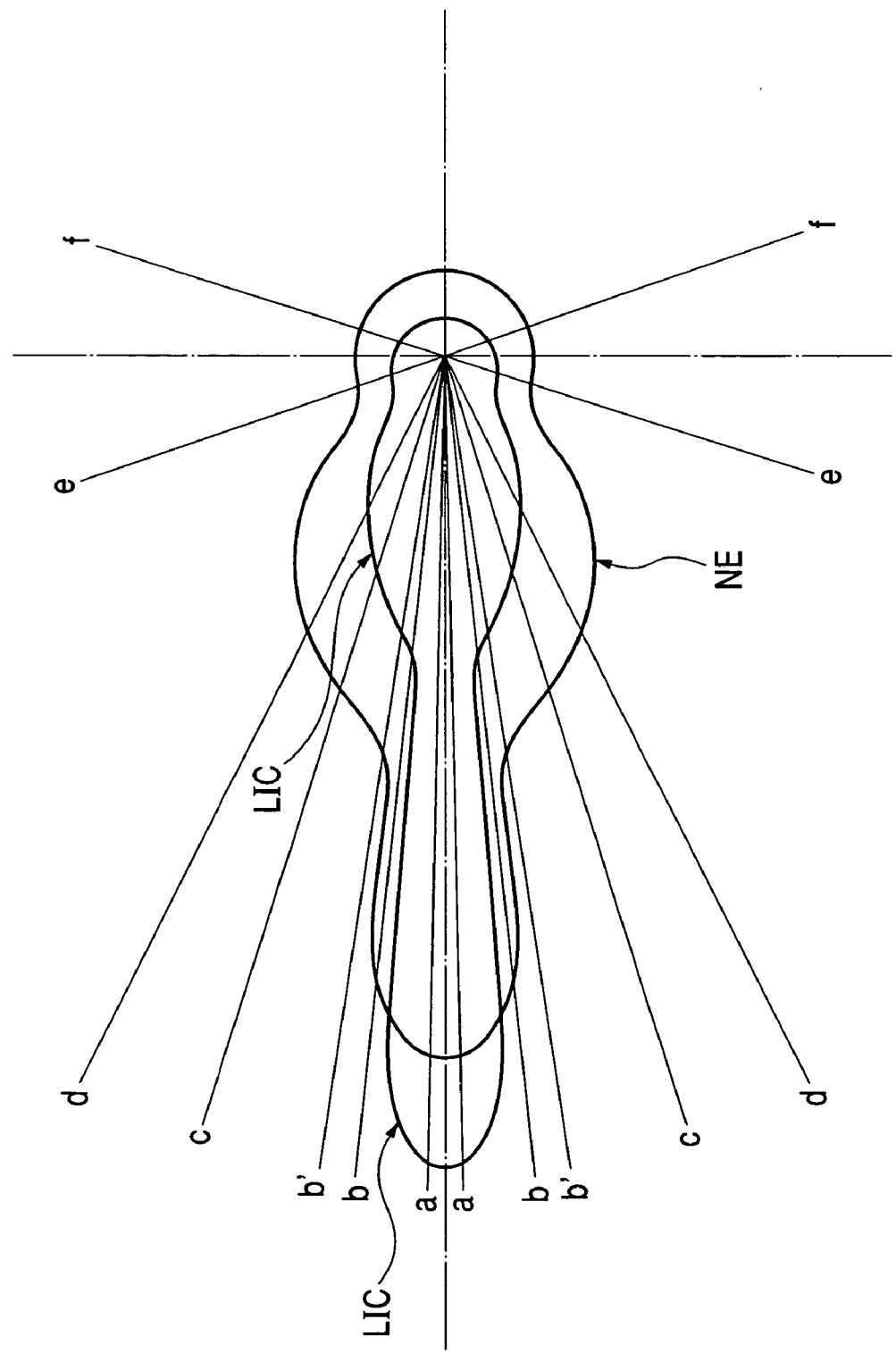
FIG. 12 shows estimated distribution of light scattered by neutrophils and large immature cells.
Figure 14A:
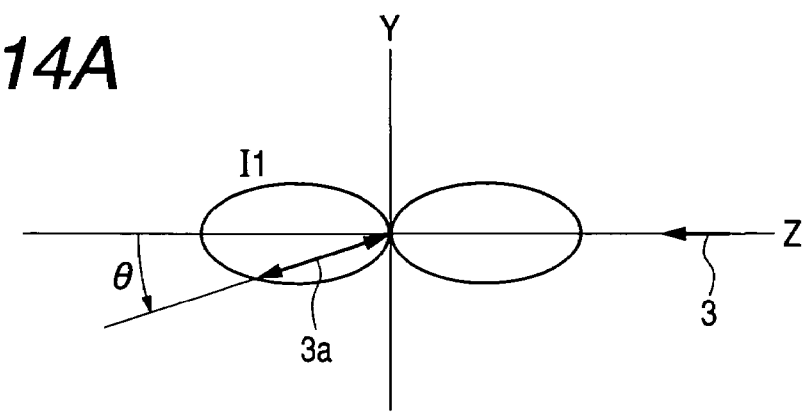
Figure 14B:
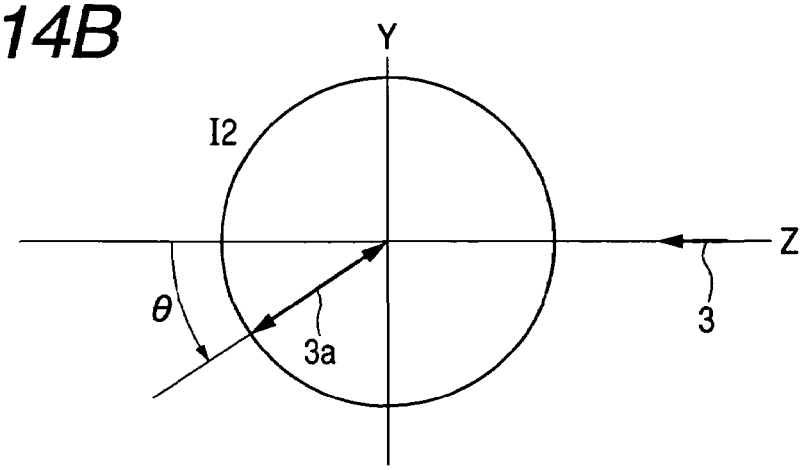
Figure 14C:
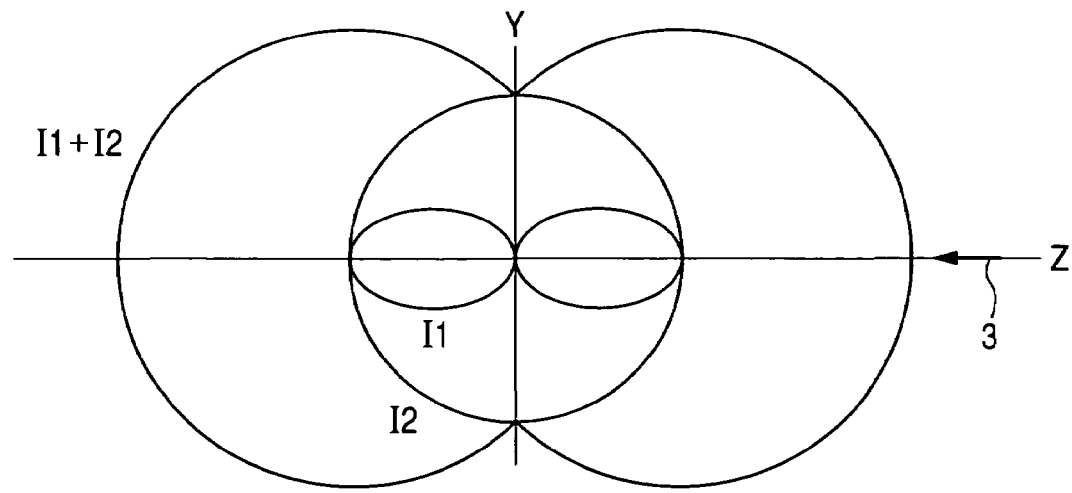
Figure 15A:
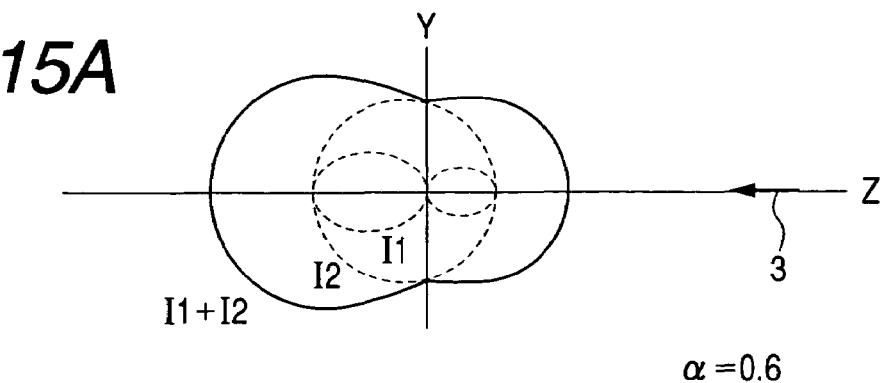
FIGS. 15A to 15D are diagrams for explaining a change in the intensity distribution of the scattered light according to a particle parameter.
Figure 15B:
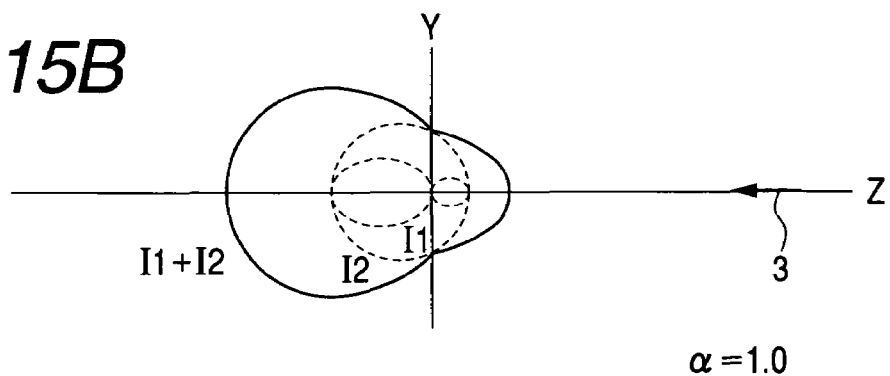
Figure 15C:
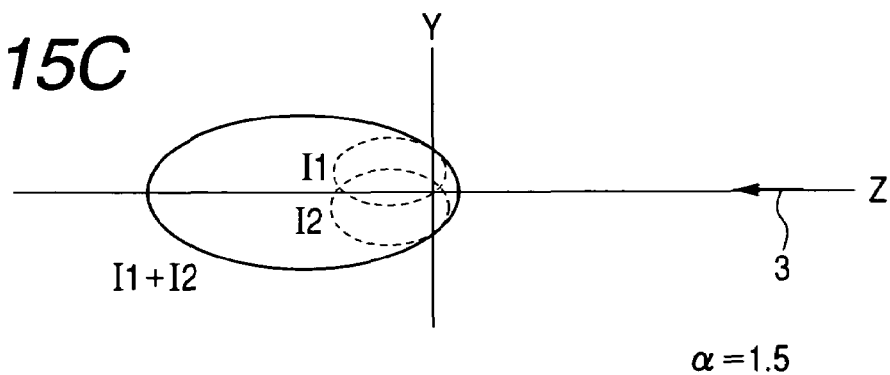
Figure 15D:
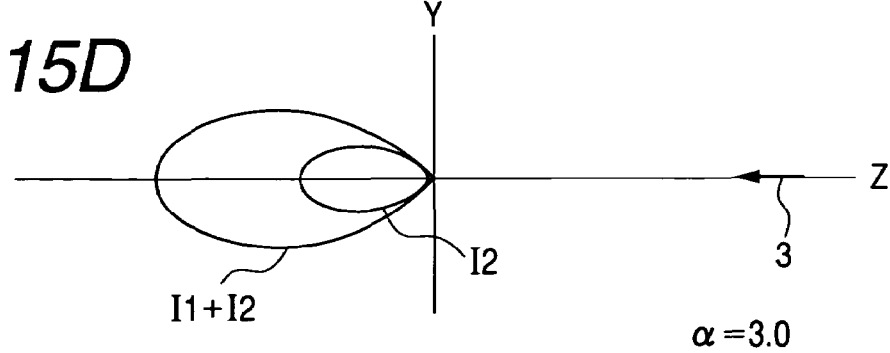
Figure 16:
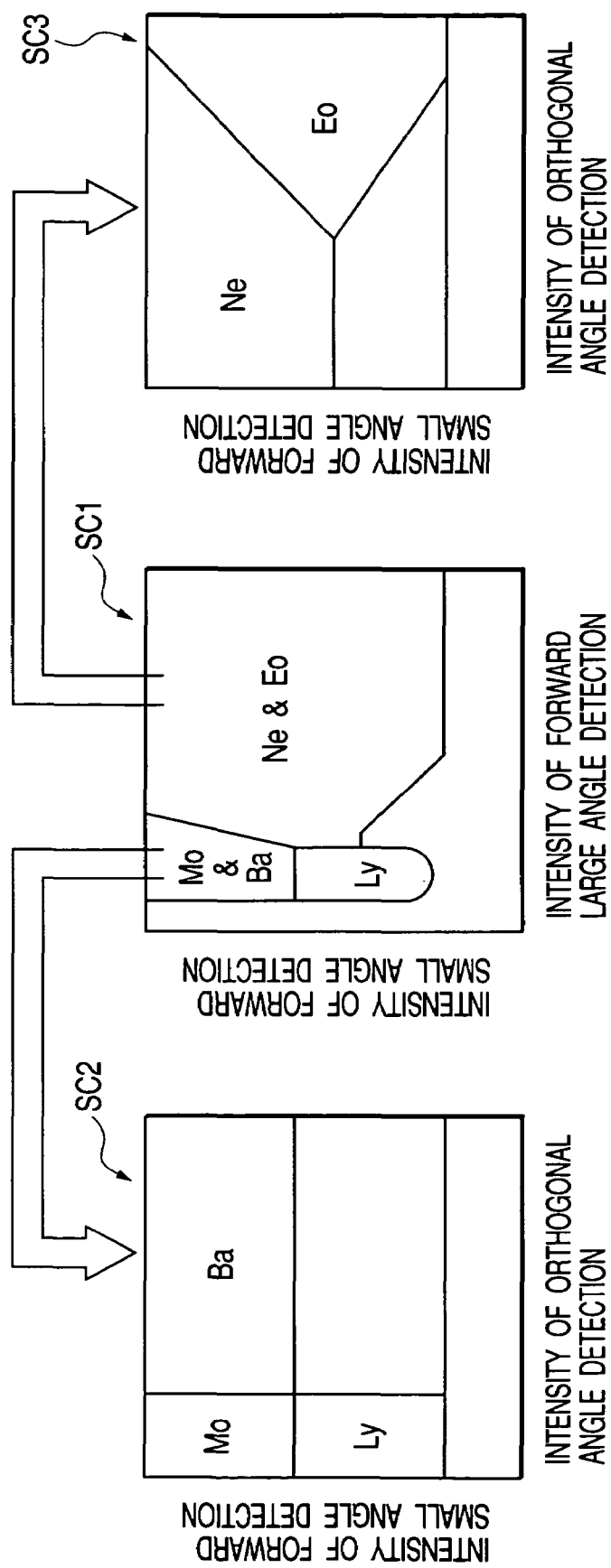
FIG. 16 are views for explaining scattergram analysis using the intensity of forward small scattered light, the intensity of forward large scattered light, and the intensity of orthogonal scattered light.

Therefore, with consideration given to the granules and particles included in various leukocyte cells, the distribution of intensities of light scattered by various leukocytes are estimated as shown in FIGS. 11 and 12.

Here, angle "a" denotes the minimum angle within the forward small scattered light detection angle range corresponding to a1 and a2 described by reference to FIGS. 4A and 5;

Angle "b" denotes the maximum angle within the forward small scattered light detection angle range corresponding to b1 and b2 described in the conditions of Table 2;

Angle "b'" denotes the maximum angle within the forward small scattered light detection angle range corresponding to b1 and b2 described in the conditions of Table 1;

Angle "c" denotes the minimum angle within the forward large scattered light detection angle range corresponding to c1, c2;

Angle "d" denotes the maximum angle within the forward large scattered light detection angle range corresponding to d1, d2;

Angle "e" denotes the minimum angle within the orthogonal scattered light detection angle range corresponding to e1, e2; and Angle "f" denotes the maximum angle within the orthogonal scattered light detection angle range corresponding to f1, f2.

The point of center O denotes the position of a blood cell. Further, angles "a," "c," "d," "e," and "f" are the same angles as in Tables 1 and 2.

FIG. 11 is a view in which the intensity distribution of monocytes, that of lymphocytes, and that of eosinophils are estimated.

A monocyte has a diameter of about 15 to 20 µm and includes a large nucleus therein. Here, many monocytes have nuclei with complicated constructions and include numerous granules.

Lymphocytes are of various sizes and include very few granules. A small lymphocyte measures 7 to 10 µm; a medium lymphocyte measures 10 to 14 µm; and a large lymphocyte measures 14 µm. Many small lymphocytes have round nuclei and include very few granules. Medium lymphocytes are classified into lymphocytes which are on the whole large, and lymphocytes which have nuclei similar to those of the small lymphocytes and include numerous cytoplasmas. Nuclei of large lymphocytes are usually located not in the center but near the edge of cytoplasmas.

In many cases, an eosinophil has two segments; on rare occasions, an eosinophil has three or more segments. A large number of special granules measuring 0.5 to 1.0 µm are present in the eosinophils.

Therefore, the distribution of light scattered by monocytes, the distribution of light scattered by lymphocytes, and the distribution of light scattered by eosinophils are created as a result of an overlap between Fraunhofer's diffraction, Rayleigh's scattering, and Mie's scattering of the nuclei and granules existing in the monocytes, lymphocytes, and eosinophils.

The distributions of the light scattered by various leukocytes will be described hereinbelow. Needless to say, the distributions include individual differences.

Monocytes are the largest cells among the leukocytes observed in normal blood. Therefore, considerable Fraunhofer's diffraction arises in the monocytes. As shown in FIG. 11, the intensity of the diffracted light is estimated to extend far in the incident direction of the laser beam.

As a result of the forward small scattered light detection angle range having been narrowed from the range described in the conditions of Table 1 to that described in the conditions of Table 2, the intensity of forward small scattered light has become slightly weak (see FIG. 6). Hence, a boundary of the distribution of light intensity due to Fraunhofer's diffraction is considered to be located outside the scattering angle "b" (i.e., the maximum angle in the forward small scattered light detection angle range shown in Table 2) and in the vicinity of the scattering angle "b'" (i.e., the maximum angle in the forward small scattered light detection angle range shown in Table 1).

Here, the intensity of forward large scattered light is about one-third the intensity of forward small scattered light (see FIG. 6), and the intensity of orthogonal scattered light is about one-ninth the same (see FIG. 10). Therefore, the area of the scattered light intensity distribution defined by the scattering angles "c" and "d" is about one-third the area of the scattered light intensity distribution defined by the scattered angles "a" and "b" and the area of the scattered light intensity distribution defined by the scattering angles "e" and "f" is about one-ninth the area of the scattered light intensity distribution defined by the scattered angles "a" and "b."

The intensity of forward small scattered light originating from the lymphocytes is about two-thirds the intensity of forward small scattered light originating from the monocytes. The intensity of forward large scattered light originating from the lymphocytes is slightly weaker than that of the monocytes. The intensity of orthogonal scattered light originating from the lymphocytes is substantially the same as that of the monocytes.

The intensity of forward small scattered light originating from the eosinophils is about two-thirds the intensity of forward small scattered light originating from the monocytes. The intensity of forward large scattered light originating from the eosinophils is about three times that of the monocytes. Moreover, the intensity of orthogonal scattered light originating from the eosinophils is about nine times that of the monocytes.

The scattered light intensity distributions in the respective detection angle ranges can be estimated on the basis of the foregoing proportions. Thus, the entire intensity distribution of light scattered by the monocytes, the lymphocytes, and the eosinophils can be estimated in consideration of continuity.

FIG. 12 is a view in which the intensity distribution of light scattered by neutrophils and the intensity distribution of light scattered by large immature cells are estimated.

Here, the neutrophils have a diameter ranging from 12 to 15 μm. The number of segments of a nucleus ranges from two to five. A large number of glycogen granules measuring 0.05 to 0.2 μm are present in the neutrophils.

The large immature cells include immature granulocytes and, in some cases, immature cells other than granulocytes.

The intensity of forward small scattered light originating from the neutrophils is substantially the same as the intensity of forward small scattered light originating from the monocytes. The intensity of forward large scattered light originating from the neutrophils is about 2.5 times that of the monocytes. Moreover, the intensity of orthogonal scattered light originating from the neutrophils is about three times that of the monocytes.

The intensity of forward small scattered light originating from the large immature cells is about 1.3 times the intensity of forward small scattered light originating from the neutrophils (see FIG. 9). However, the distribution is separated from other distributions to such an extent that the distribution can be sufficiently identified. The intensity of forward large scattered light originating from the large immature cells is about one-half that of the neutrophils.

The scattered light intensity distribution in the respective detection angle ranges can be estimated on the basis of the above-described proportions. Thus, the entire intensity distribution of light scattered by the neutrophils and large immature cells can be estimated in consideration of continuity.

As shown in the scattergrams SCB and SCB', the forward small scattered light detection angle range provided in Table 2 has been improved. As a result, separation of monocytes and lymphocytes on the scattergram is improved. As shown in FIG. 11, the supposed reasons for this are that the maximum angle (i.e., the angle "b") in the forward small scattered light detection angle range is set at a position sufficiently inside in relation to the boundary of the light intensity distribution of monocytes due to Fraunhofer's diffraction, and that the intensity of light scattered by lymphocytes accounts for the scattered angle range b to b', which is larger than that which the intensity of light scattered by monocytes accounts for.

The maximum angle in the forward small scattered light detection angle range is set such that the intensity of the forward small scattered light of monocytes whose forward small scattered light intensity is lowest among those of all the monocytes becomes sufficiently greater than the forward small scattered light intensity of lymphocytes whose forward small scattered light intensity is highest among those of all the lymphocytes. As a result, the monocytes and the lymphocytes can be sufficiently separated from each other as shown in the scattergrams SCB and SCB'.

Consequently, further separation of monocytes and lymphocytes becomes possible by setting the angle toward a more inner position. However, if the angle is made excessively small, the forward small scattered light intensity becomes too low. Hence, a tradeoff between separation of two types of blood cells and assurance of a scattered light intensity level must be taken into consideration.

As shown in the scattergrams SCB and SCB', separation between neutrophils and eosinophils is also improved. The supposed reasons for this are that: i) the scattered light intensity distribution of neutrophils owing to Fraunhofer's diffraction is analogous to that of monocytes, ii) the maximum angle (angle "b") in the forward small scattered light detection angle range is set at a position sufficiently inside relative to the boundary of the light intensity distribution of neutrophils owing to Fraunhofer's diffraction, and iii) the scattered light intensity which eosinophils account for in the scattering angle range b to b' is higher than the scattered light intensity which neutrophils account for.

The maximum angle in the forward small scattered light detection angle range is set such that the intensity of the forward small scattered light of neutrophils whose forward small scattered light intensity is lowest among those of all the neutrophils becomes sufficiently greater than the forward small scattered light intensity of eosinophils whose forward small scattered light intensity is highest among those of all the eosinophils. As a result, the neutrophils and the eosinophils can be sufficiently separated from each other as shown in the scattergrams SCB and SCB'. This tendency is considered to appear more noticeable by narrowing the maximum angle in the forward small scattered light detection angle range.

As shown in FIG. 9, there is improved a tendency for separation between the distribution of neutrophils that is plotted on the scattergram while the normal blood is taken as a sample and the distribution of large immature cells that is plotted on the scattergram while the blood including large immature cells is taken as a sample. Consequently, neutrophils can be distinguished from large immature cells by setting an appropriate threshold value Th (see FIG. 9) and determining an area where the distribution is present from among areas separated by the threshold value. Depending on a patient's symptoms, neutrophils and large immature cells may coexist in a blood sample. Even in such a case, the neutrophils and the large immature cells can be classified through use of an appropriate threshold value.

The reason for this is that the scattered light intensity which neutrophils account for in the scattering angle range b to b' is higher than the scattered light intensity which large immature cells account for.

Thus, it is useful to determine a scattered light detection angle range to be used for classifying blood cells in consideration of the scattered light intensity distributions which differ according to the type of blood cells, by measuring the intensity of light scattered by various blood cells, and estimating the scattered light intensity distribution of the blood cell from the measured values.

By adoption of such a method, an appropriate scattered light detection angle range can be determined even when a slight variation exists in components of a reagent to be used for processing a sample flow.

This method is not limited to blood cells and can also be applied to other particles.

What is claimed is:

1. A flow cytometer, comprising:
a flow cell, through which a blood sample containing leukocytes flows;
a light source, which emits a light beam in a first direction, the light beam to be incident into the flow cell and scattered by the blood sample as scattered light;
a first detector, which detects an intensity of forward small scattered light out of the scattered light, the first detector arranged so as to have a maximum angle of a detection angle range for the forward small scattered light stemmed from the first direction at a position outside of the flow cell, which is 4 degrees or less;
a second detector, which detects an intensity of forward large scattered light out of the scattered light; and
a processor, which classifies the leukocytes so as to prepare a scattergram in which monocytes and lymphocytes contained in the blood sample are distinguishably distributed on a plane defined by a first axis associated with the detected intensity of the forward large scattered light and a second axis associated with the detected intensity of the forward small scattered light.

2. A flow cytometer, comprising:
a flow cell, through which a blood sample containing leukocytes flows;
a light source, which emits a light beam in a first direction, the light beam to be incident into the flow cell and scattered by the blood sample as scattered light;
a first detector, which detects an intensity of forward small scattered light out of the scattered light, the first detector arranged so as to have a maximum angle of a detection angle range for the forward small scattered light stemmed from the first direction at a position outside of the flow cell, which is 4 degrees or less;
a second detector, which detects an intensity of forward large scattered light out of the scattered light; and
a processor, which classifies the leukocytes so as to prepare a scattergram in which neutrophils and eosinophils contained in the blood sample are distinguishably distributed on a plane defined by a first axis associated with the detected intensity of the forward large scattered light and a second axis associated with the detected intensity of the forward small scattered light.

3. A flow cytometer, comprising:
a flow cell, through which a blood sample containing leukocytes flows;
a light source, which emits a light beam in a first direction, the light beam to be incident into the flow cell and scattered by the blood sample as scattered light;
a first detector, which detects an intensity of forward small scattered light out of the scattered light, the first detector arranged so as to have a maximum angle of a detection angle range for the forward small scattered light stemmed from the first direction at a position outside of the flow cell, which is 4 degrees or less;
a second detector, which detects an intensity of forward large scattered light out of the scattered light; and
a processor, which classifies the leukocytes so as to prepare a scattergram in which neutrophils and large immature cells contained in the blood sample are distinguishably distributed on a plane defined by a first axis associated with the detected intensity of the forward large scattered light and a second axis associated with the detected intensity of the forward small scattered light.

4. A flow cytometer, comprising:
a flow cell, through which a blood sample containing leukocytes flows;
a light source, which emits a light beam in a first direction, the light beam to be incident into the flow cell and scattered by the blood sample as scattered light;
a first detector, which detects an intensity of forward small scattered light out of the scattered light, the first detector arranged so as to have a maximum angle of a detection angle range for the forward small scattered light stemmed from the first direction at a position outside of the flow cell, which is 4 degrees or less;
a second detector, which detects an intensity of forward large scattered light out of the scattered light, the second detector arranged so as to have a detection angle range for the forward large scattered light stemmed from the first direction at a position outside of the flow cell, which falls in a range from 10 degrees to 16 degrees; and
a processor, which classifies the leukocytes based on the detected intensity of the forward large scattered light and the detected intensity of the forward small scattered light.

* * * * *